United States Patent [19]
Gordon

[11] Patent Number: 4,880,638
[45] Date of Patent: Nov. 14, 1989

[54] BIOCIDAL COMPOSITION AND METHOD FOR DISINFECTING ARTICLES

[75] Inventor: Gordon, Gilbert, Oxford, Ohio

[73] Assignee: Bioxy International, Ltd., Fort Worth, Tex.

[21] Appl. No.: 235,378

[22] Filed: Aug. 23, 1988

[51] Int. Cl.$^4$ .................... A01N 39/00; A01N 59/00; A01N 59/08; A01N 59/14

[52] U.S. Cl. .................... 424/662; 424/616; 424/660; 424/661; 424/663; 424/665; 424/715

[58] Field of Search ............... 424/149, 130, 662, 616, 424/660, 661, 663, 665, 715

[56] References Cited

U.S. PATENT DOCUMENTS

| | | | |
|---|---|---|---|
| 2,379,335 | 3/1941 | Montclair | 424/149 |
| 2,575,670 | 11/1951 | MacMahon | 424/149 |
| 3,585,147 | 6/1971 | Gordon | 252/187 |
| 3,873,696 | 3/1975 | Randeri et al. | 424/162 |
| 4,201,756 | 5/1980 | Saeman et al. | 424/149 |
| 4,296,103 | 10/1981 | Laso | 424/149 |
| 4,317,814 | 3/1982 | Laso | 424/149 |
| 4,574,084 | 3/1986 | Berger | 424/128 |
| 4,690,772 | 9/1987 | Tell et al. | 424/149 |

Primary Examiner—Allen J. Robinson
Attorney, Agent, or Firm—Hubbard, Thurman, Turner & Tucker

[57] ABSTRACT

This invention relates to a biocidal composition comprising water, a source of chlorite ions, a source of chloride ions and a source of chlorate ions where the mol ratio of chlorite ions to chlorate ions is in the range from about 2:1 to about 1000:1, the mol ratio of chlorite ions to chloride ions is from about 0.1:1 to about 1000:1 and the mol ratio of chloride ions to chlorate ions is in the range from about 0.1:1 to about 1000.1; the chlorite ion source present in amounts of from about 40 grams to about 0.04 milligrams per thousand grams of water; and the composition including a pH adjusting material in an amount sufficient to adjust the pH of the mixture to above 7.0. Thus the composition avoiding the formation of significant amounts of chlorine dioxide or stabilized chloride dioxide.

15 Claims, No Drawings

BIOCIDAL COMPOSITION AND METHOD FOR DISINFECTING ARTICLES

BACKGROUND OF THE INVENTION

This invention relates to a biocidal composition. In another aspect, the invention relates to a method for disinfecting articles by contacting the article with a composition that forms on mixing various chlorine containing compounds with water.

It has long been known that various chlorine containing compounds can be used as biocidal agents. Indeed, the literature contains many references to the use of chlorine gas, various chlorites and even chlorine dioxide as materials that can be used to kill microorganisms. Chlorine dioxide has been suggested as a strong oxidizing agent that is especially useful to kill various microorganisms.

The prior art describes many processes for the direct use of chlorine dioxide for use as a biocide. The prior art also described many processes for the production of stabilized chlorine dioxide by the addition of a variety of inorganic compounds such as inorganic boron and/or various peroxides, including hydrogen peroxide.

In spite of the large number of prior art references to chlorine dioxide, it has many short comings because it is a potentially hazardous material and is generally difficult to produce and apply where needed. Chlorine dioxide is also corrosive and its formation requires considerable amounts of acid which add to its corrosive properties.

Chlorine dioxide has been used in the treatment of water supplies and in swimming pools. In may cases, chlorine dioxide has been shown to be superior to chlorine as a bactericide. On the other hand, chlorine dioxide is dangerous to handle, cannot be stored and is explosive in the concentrated gaseous state.

In a summary entitled "THE CHEMISTRY OF CHLORINE DIOXIDE", Messrs. Gilbert Gordon, Robert G. Keiffer and David M. Rosenblatt "Progress in Inorganic Chemistry", Volume XV, S. L. Lippard, Editor John Wiley & Sons, New York, N. Y., 1972; pages 201–286, have shown a collection of 230 references related to chlorine dioxide. There are several United States Patents such as U.S. Pat. Nos. 3,123,521 and 4,104,190, relating to chlorine dioxide. U.S. Pat. No. 3,123,521 describes a stabilized chlorine dioxide as a commercial germicide using sodium carbonate peroxide. U.S. Pat. No. 4,104,190 describes difficulties with the prior art requiring a highly acid environment for generation of chlorine dioxide from chlorine dioxide precursors; for example in pH's of 2–3 or lower; and then describes a method of employing a chlorine emitter to effect production of chlorine dioxide at pH's in the range of 4–9. There is a wide variety of U.S. Patents relating the chlorine dioxide in a variety of uses.

Chlorine dioxide has been demonstrated to be an effective microbicide, for example, in the paper industry and in textile bleaching where it is also known to be a powerful and effective oxidizing agent. Prior art references such as U.S. Pat. Nos. 4,296,102 and 4,296,103 to Laso, U.S. Pat. No. 4,330,531 and Re. 31,779 to Alleger and U.S. Pat. No. 4,507,285 to Kuhne describe the use of chlorine dioxide and or stabilized aqueous solutions of chlorine dioxide.

The stabilized aqueous solutions of chlorine oxides contain chlorine dioxide as well as other dissolved oxides reported in the above patents of chlorine. In addition these solutions usually contain a peroxide, percarbonate or other oxygen donor. An essential ingredient of the Laso and Alleger patents is the presence of stabilized aqueous solutions of chlorine oxide utilizing oxygen donors.

Laso describes the preparation of solutions in his invention where chlorine dioxide may be added as a gas or formed in situ in the aqueous media. Laso reports that the chlorine dioxide is believed to be held in the form of a labile complex with a special boron compound resulting in a stabilized chlorine dioxide composition.

The usual method for using or incorporating chlorine dioxide gas is to dissolve or generate the gas to form a solution following which it is used as a bactericide.

Moreover, Alliger reports that the chlorine dioxide accelerates the metabolism of the bacterial cell to the detriment of the cell growth. Alliger also indicates that yet other credible authorities assert that the chlorine ion in chlorine dioxide goes through as many as eight possible oxidation states in passing through a pore wall. Furthermore, chlorine dioxide purportedly destroys and breaks down the cell until water is lost from the protoplasm and thereafter completely destroys or oxidizes the cell. In each of these cases the compositions are used in a relatively wide concentration range, but in every case they require the production of and/or presence of chlorine dioxide itself.

The solutions of this invention contain little or no chlorine dioxide or stabilzed chlorine dioxide. Instead solutions are disclosed which exhibit biocidal synergism which is developed between the chlorite ion, the chlorate ion and chloride ion when mixed in accordance with the procedures and in the ratios described herein. As will be more fully discussed hereafter, the instant disclosure provides for mixing various components so as to provide a "redox buffered" equilibrium of intermediate species that are extremely effective as biocidal agents. In other words, the instant invention is aimed at the formation of such intermediate species instead of the production of chlorine dioxide as taught by the prior art.

In view of the foregoing, it is readily apparent that it is desirable to have improved biocidal compositions that are safe and easy to prepare. It is also readily apparent that it is desirable to have improved methods of disinfecting various articles with very high kill rates of microorganisms. It is also highly desirable to have stable biocidal compositions that can be stored over long periods of time without appreciable loss of their biocidal properties.

SUMMARY OF THE INVENTION

Accordingly, it is an object of this invention to provide an improved composition that has outstanding biocidal properties. It is yet another object of this invention to provide an improved method of disinfecting articles by contacting the article with an improved biocidal composition.

It is yet another object of this invention to provide a combination of stable chlorine containing components that contain little or no chlorine dioxide or solutions of complexed chlorine dioxide (i.e. stabilized chlorine dioxide). It is still a further object of this invention to provide a series of synergistic combinations of chlorine containing materials that are effective as microbicides, virosides and sporocides without utilizing chlorine dioxide itself. These and other objects will become apparent from the invention described hereinafter.

It has now been found that a composition which forms on mixing water, a source of chlorite ions, a source of chloride ions and a source of chlorate ions is a highly effective biocidal composition. The composition can include additional components to improve the stability of the composition so it may be stored for long periods of time without losing its biocidal properites. The composition can also contain additional components to selectively increase its biocidal properties in certain environments.

In the prior art, chlorine dioxide is the demonstrated microbial agent and the patents describe inventions to stabilize or to produce chlorine dioxide. Indeed, the prior art teaches the actual production of chlorine dioxide and extolls its properties. In contrast, this invention is directed to mixtures of components which desirably do not produce large amounts of chlorine dioxide and which regenerate premicrobial interactive chemical reagents by recycling the reactants by means of a carefully balanced synergistic redox equilibrium process hitherto unreported.

The compositions of this invention provide redox buffered stoichiometric solutions which contain little or no chlorine dioxide or so called "stabilized" chlorine dioxide. Highly sensitive analytical measurements have been used which would detect as low as 1 ppm (parts per million) of chlorine dioxide or chlorine dioxide containing complexes in the solutions of this invention and no chlorine dioxide was detected. Instead this invention describes a synergistic combination of safe chlorine compounds which when mixed in a specific range of ratios results in unexpected microbial properties without the necessity to produce chlorine dioxide per se.

Many patents teach that chlorine dioxide is an effective microbicide and that it is also a powerful and effective oxidizing agent. Thus, there is a wide variety of patents and prior art references which describe the production of chlorine dioxide and/or the use of stabilized chlorine dioxide solutions. This prior art has not shown that the compositions described herein can be equally or even more effective as microbicides, virosides and sporocides.

In contrast to other inventions describing chlorine dioxide, this invention does not require chlorine or chlorine dioxide in order to act as a microbial killer agent. The unexpected synergism described herein is as a result of specific ratios of inorganic chlorine containing species, without the necessity to produce chlorine dioxide and/or stabilized chlorine dioxide.

It has now been found that a composition which forms on mixing specific materials has an unexpectedly high biocidal effectiveness. This composition forms on mixing water, a source of chlorite ions and a source of chlorate ions where the mole ratio of chlorite ions to chlorate ions is in the range of from about 2:1 to about 1000:1. This composition also requires chloride ion where the ratio of chlorite ion to chloride ion is at least about 0.1:1 but may be as large as 100:1. In addition, the chloride ion to chlorate ion ratio must be at least 0.1:1 but may be as great as 1000:1. This combination of chlorite ion, chlorate ion and chloride ion results in the synergism heretofore unreported and undocumented.

Test populations of living cells were selected to demonstrate the broad application of the cell killing ability of compounds taught by this invention. Bacteria populations were selected as demonstration models because bacteria cells reproduce and divide into new cells in time intervals in the order of minutes and hours, rather than days or weeks. It is also possible with current technology to know exactly how many bacteria cells are in a growth medium, and how many are dividing at any instant. At an exact time, a specific concentration of a candidate cell kill chemical or chemicals can be put into contact with the bacteria cells. The contact period can be controlled precisely.

Three bacteria types were chosen for demonstration. Each genus selected differs from the other two in morphology and utilization of chemical substrates for cell growth and cellular metabolism. *Serratia marcescens* is a Gram-negative facultatively anaerobic rod. *Staphylococcus epidermidis* is a Gram-positive facultatively anaerobic coccus which requires amino acids in its growth substrate. *Pseudomonas aerugenosa* is a strictly nonfermentative (respiratory only) facultative chemoorganotrophic, motile, Gram-negative rod, which is known to be able to utilize over 80 different organic subtrates and either hydrogen and carbon monoxide as energy sources alternate to oxygen. The demands for nutrition, growth and metabolism of these living cells are clearly different, however the killing speed and concentration of compound needed has been shown to be independent of cell type.

Microbiological studies using the compositions of this invention have been conducted with three bacteria (*Serratia marcescens* ATCC Number 14041, *Staphylococcus epidermidia* ATCC Number 17917 and *Pseudomonas aeruginosa* ATCC Number 9027). These studies showed that with all three bacteria, no growth was noted nineteen hours after treatment. In other words, the instant composition was shown to be completely effective, even at 1 to 1000 dilutions, in being able to inhibit appropriate bacterial growth. This indicates that the compositions of the instant invention are bactericidal rather than merely bacteriostatic in action. Furthermore, the instant compositions appeared to be acting in a way which effects all bacteria cells, with even the most resistive succumbing after a longer period of time than those which are most sensitive to the chemical preparations.

Additional results showed that the instant composition was able to make both a rapid and an absolute kill of *salmonella sp.* and *camplyobacter fetus ssp. Jejuni*. Subculture dilutions of the samples were also performed after just 10 minutes of exposure. The subcultures revealed no growh, i.e. all bacteria succumbed to the action of the synergistic instant compound.

DESCRIPTION OF PREFERRED EMBODIMENTS

The instant invention provides for a composition that has outstanding biocidal properties. The composition forms on mixing water with a source of chlorite ions, a source of chloride ions and a source of chlorate ions. The compositions should have a mol ratio of chlorite ions to chlorate ions in the range of from about 2:1 to about 1000:1, a ratio of chlorite ions to chloride ions of from about 0.1:1 to about 1000:1 and a ratio of chloride ions to chlorate ions in the range of from about 0.1 to 1 to about 1000:1. By forming such a composition, it can then be applied to various articles to kill microorganisms in an on such articles. The stability of the composition can be improved by adding an appropriate pH adjusting material to adjust the resulting admixture to a pH above about 7.5.

In preparing the compositions of this invention, various commercially available materials are utilized as the starting materials. For example, the source for the chlorite ions can include materials such as alkali metal chlorites and the like. Sodium chlorite is especially useful in preparing the compositions of this invention because of its availability and because of its solubility in water. Other suitable sources for the chlorite ions include the alkali metal chlorites and the alkaline earth metal chlorites, as well as ammonium chlorite.

Suitable sources for the chlorate ion include various commercially available chlorates with alkali metal chlorates being preferred. It has been found that sodium chlorate and potassium chlorate are especially useful in producing the compositions of this invention because of their solubility and availability. Other sources of the chlorate ions include the alkaline earth metal chlorates and ammonium chlorate.

Suitable sources of the chloride ion include various commerically available chloride with alkali metal chlorides being preferred. Sodium chloride and potassium chloride are especially useful because of their cost and solubility. Alkaline earth metal chlorides and ammonium chlorides can also be used.

In preparing the compositions of this invention, sufficient water should be available to dissolve the starting materials. While water is an essential ingredient, it should be understood that other solvents can also be present such as various alcohols, glycols and the like. It has been found that water should be present in an amount of at least 0.1 gram mols per liter.

In order for the compositions to have good biocidal properties the amount of the chlorite ion source should be sufficient to provide at least $10^{-6}$ gram mols per liter of chlorite ion.

The mol ratio of chlorite ions to chlorate ions that are added to the water containing solvent should be in the range of from about 2:1 up to about 1000:1. A preferred range of chlorite ion material to chlorate ion material that is added to the water containing solvent is in the range of from about 3:1 to about 500:1.

While the broad range of chlorite ions to chloride ions is from about 0.1:1 to about 1000:1, a more preferred range is from about 1:1 to about 50:1.

The broad range of chloride ions to chlorate ions is from about 0.1:1 to about 1000:1 and the preferred range is from about 3:1 and to about 10:1.

It should be understood that the amount of the chlorite ion materials and the chlorate ion materials that are added to the water containing solvent can be up to a point where the solvent material is completely saturated. In some instances, it may be desirable to gently heat the mixture of materials to assist in dissolution.

The stability of the compositions of this invention can be improved by adding a pH adjusting material to the composition to adjust the pH of the resulting mixture to a pH above 7. Preferably the pH will be adjusted to above 7.5. The concentration of the buffer can range from 0.001 molar up to the saturation level of the solution. The preferred buffering materials contain borate or phosphate salts. Preferred buffer concentration is in the range of 0.001 molar to 0.5 moles. It has been found that if the pH is adjusted to a pH of about 13 that the compositions are very stable and will retain their biocidal properties over long periods of storage. Various pH adjusting materials such as alkali metal hydroxides and the like are preferred. Other pH adjusting materials that can be utilized in this invention include buffers containing inorganic anions such as phosphates, sulfates, borates and the like.

It has been found that various other materials can be added to the compositions of this invention to improve their efficacy. For example, it has been found that the addition of materials such as hydrogen perioxide will inhibit the production of chlorine dioxide. While it has long been known that chlorine dioxide does have certain biocidal properties, the compositions of this invention have improved biocidal properties when compared with the biocidal properties of chlorine dioxide. Indeed, because of the dangerous and potentially poisonous properties of chlorine dioxide, it is desired to minimize the amount of chlorine dioxide in products that may be formed when the compositions of this invention are applied to various articles to kill micoorganisms on or in such articles. Various other materials such as borates, perborates and percarbonates can also be utilized to retard the formation of chlorine dioxide. Such materials include borax, and various peroxides such as hydrogen peroxide, peroxysulfate and peroxyborate and peroxydisulfate.

In preparing the compositions of this inventionn, a very simple procedure can be followed whereby the chlorite ion source and the chlorate ion source mixed with the water containing solvent and allowed to dissolve therein. Following this procedure, the various other materials can be added to the resulting solution. It has been found that the mixing can take place under any desirable temperature and pressure so long as the starting materials are dissolved in the water containing solvent. Following the mixing, in most instances a precipitate will form from heavy metal impurities in the starting materials. In order to improve the stability of the compositions of this invention, the clear liquid should be decanted or filtered to remove such precipitates.

Once the compositions of this invention have been formulated, they can be utilized to disinfect various articles by contacting the article with the composition.

Although it is not the intention to be limited to any theory of operation or mechanism, it is believed that the biocidal compositions that are formed by mixing the aforementioned ingredients are some type of reaction product or intermediate product that is highly effective in killing various types of organisms. As will be appreciated by those skilled in the art, such intermediate products of course can be "pushed" to produce final reaction products. In this instance, it is possible that the various materials that are combined together can be "pushed" to produce final reaction products that include significant amounts of chlorine dioxide. However, it has been found that by controlling and limiting the amount of chlorine dioxide that is actually formed, the intermediate products are indeed more effective in a killing organisms than chlorine dioxide itself. Therefore, the theory or mechanism, as now believed, centers around the combination of the aforementioned materials to form highly active intermediate products without the necessary production of chlorine dioxide. Thus, the instant invention differs from the prior art by controlling or preventing the formation of significant amounts of chlorine dioxide.

In some instances, it may be desirable to add additional materials to the aforementioned solutions to aid in the formation of the highly active intermediate products. To aid in an explanation of the theory of mechanism, as it is now understood, such materials are referred to as "triggering agents". It is presently believed that such materials will "trigger" the bicidal properties of the compositions to increase the formation of the desired intermediate products. Such triggering agents include various materials such as inorganic acids, either alone or in combination with various borates, oxidizing agents such as hypochlorous acids, chlorine gas and the like, as well as various transition metal ions. Such transition metal ions include such materials as compounds that contain iron ions.

When inorganic acids are utilized as a triggering agent, such inorganic acids will include chloride, sulfuric acid, phosphoric acid and the like. Such inorganic acids, as mentioned above, can be used alone or in combination with boric materials including various alkali metal borates such as sodium borate, potassium borate and the like. It has been found that the addition of the borate materials will inhibit the chlorine dioxide formation. Oxidizing agents such as hypochlorous acid, chlorine and various other oxidizing agents are also useful as triggering agents. Mixtures of the triggering agents can also be used.

In some instances, it has been observed that living organisms such as bacteria, fungi and the like also serve as triggering agents. While the exact mechanism of such living organisms serving as triggering agents is not known, it is believed that the surfaces of the living organisms somehow cause the compositions of this invention to generate reaction products having enhanced biocidal properties without the formation of excessive amounts of chlorine dioxide. It should also be appreciated that while the foregoing discussion is directed to biocidal compositions, the desired biocidal properties may be accomplished by the compositions forming a metabolic block in the critical life providing pathway.

In those instances where triggering agents are utilized, the compositions of this invention can merely be mixed with the triggering agent at or near its time of use to enhance the biocidal properties of the compositions while exhibiting or preventing the formulation of chlorine dioxide. It should be understood however, that if great amounts of materials are added to the solutions of the present invention so as to depress the pH of the solutions to very low levels, such additions of the materials may cause the undesired formation and liberation of chlorine dioxide.

In order to demonstrate the properties of the biocidal compositions of the instant invention, the following examples are offered. It should be appreciated that these are merely examples to show the utility and effectiveness of some of the compositions of the instant invention. The inclusion of these examples should not be interpreted in any manner as limiting to the scope of the present invention to the conditions set forth in the examples.

EXAMPLE I

A biocidal composition was prepared by dissolving 950 grams of sodium chlorite in 12 liters of water. The mixture was stirred well until all of the solid dissolved. 300 grams of sodium chlorate and 350 grams of sodium chloride were then added to the aqueous mixture and it was stirred for approximately 10 minutes until all of the solids had dissolved. After mixing the solution, the solution was allowed to stand for 20 minutes and then 25 grams of sodium borate and 25 grams of sodium sulfate were added. 20 grams of hydrogen peroxide were then added to the solution. The pH of the mixture was adjusted to 13.0 by slowly adding sodium hydroxide to the solution. Once the pH was adjusted to 13.0, the solution was mixed well and allowed to stand overnight. The next morning the pH was readjusted to 13.0 by adding a small amount of sodium hydroxide. The solution was stored for 4 weeks and a very small amount of solids were observed to have settled from the solution. The clear supernatant was then decanted for use as a biocidal material. The composition of the final supernatant material had a density of 1.08. The chlorite ion was present in an amount of 0.54 mols per liter. The chlorate ion was present in the amount of 0.15 mols per liter and the chloride ion was present in an amount of 0.33 mols per liter.

EXAMPLE II

A composition that was prepared in Example I was utilized to demonstrate its effectiveness in killing salmonella enteriditis (wild type). The composition was used in an undiluted form and was diluted tenfold by the addition of water. In both of the tests, multiple colonies of the test organism grown on Mueller-Hinton agar for 24 hours at 35 degrees C. were inoculated into a Mueller-Hinton broth. A mid-log phase broth culture was prepared by incubating the inculated Mueller-Hinton broth at 35 degrees C. and at 200 rpm (shaking incubator) for 3-4 hours until the culture turbidity equals that of a number one MacFarland standard. An aliquot (0.2 ml) of the initial organism suspension was removed and serially diluted in saline (tenfold) and aliquots (0.1 ml) of the dilutions are subcultured and spread onto chocolate agar for enumberation. A 0.1 ml volume of the organism suspension was then added to the composition prepared in Example I and a tenfold dilution of such composition. After 1 hour of incubation at 35 degrees C., the mixtures were serially diluted (tenfold) and were subcultured onto Mueller-Hinton agar for enumeration using calibrated micropipette droppers. All inoculated agar plates were incubated for 35 degrees C. for 48 hours. At the end of the incubation period, complete kill was observed. Agar plates inoculated with only the organism suspension showed vigorous cell growth.

EXAMPLE III

The composition of Example I was tested to determine its effectiveness in killing *Campylobacter fetus ssp. jejuni* (wild type strain). In this procedure, the composition of Example I and a tenfold dilution of the composition were utilized. In the series of tests, the composition of the diluted composition were mixed in volumes of 0.3 ml each with 2.7 ml of thioglycollate broth. Multiple colonies of the test organism grown on chocolate agar for 48 hours at 42 degrees C. in microaerophilic bags (5% oxygen) were suspended in the broth. The suspension was ready to inoculate in the test composition when the culture turbidity equaled that of a number one MacFarland standard. A 0.1 ml volume of the organism suspension was added to a 1.9 ml volume of the test compounds. An aliquot of 0.2 ml of the organism suspension was removed and serially diluted (tenfold) in the broth and aliquots of 0.1 ml of the dilution are subcultured and spread onto chocolate agar for enumeration. After 10 minutes of incubation at 25 degrees C., 0.2 ml aliquots were removed from the compound-supplemented broth and using calibrated micropipette droppers 0.05 ml of the dilutions were subcultured on chocolate agar for enumeration. All of the inoculated agar plates were incubated at 42 degrees C. for 48 hours in microaerophilic bags. In both tests, complete kill of the organism were observed. Agar plates inoculated with only the organism suspension showed vigorous cell growth.

I claim:

1. A biocidal composition comprising water, a source of chlorite ions, a source of chloride ions and a source of chlorate ions where the mol ratio of chlorite ions to chlorate ions is in the range from about 2:1 to about 1000:1, the mol ratio of chlorite ions to chloride ions is from about 0.1:1 to about 1000:1 and the mol ratio of chloride ions to chlorate ions is in the range from about 0.1:1 to about 1000:1; the chlorite ion source present in amounts of from about 40 grams to about 0.04 miligrams per thousand grams of water; and the composition including a pH adjusting material in an amount sufficient to adjust the pH of the mixture to above 7.0.

2. The composition of claim 1 wherein water is present in an amount of at least 0.1 gram mols per liter.

3. The composition of claim 1 wherein sufficient water is available to dissolve the chlorite ion source, the chloride ion source and the chlorate ion source.

4. The composition according to claim 3 wherein the water can be combined with other solvents capable of dissolving the chlorite ion source, the chloride ion source and the chlorate ion source.

5. The composition according to claim 1 wherein said source of chlorite ions is an alkali metal chloride, said source of chloride ions is an alkali metal chloride and said source of chlorate ions is an alkali metal chlorate.

6. The composition according to claim 3 wherein said alkali metal chlorite is sodium chlorite, said alkali metal chloride is sodium chloride and said alkali metal chlorate is sodium chlorate.

7. The composition according to claim 1 wherein said composition additionally includes a material to retard the formation of chlorine dioxide, the material being selected from the group consisting of peroxides, borates, perborates, and percarbonates.

8. The composition according to claim 7 wherein said material is hydrogen peroxide.

9. A method of killing microorganisms on an article by contacting said article with an effective amount of the composition of claim 1.

10. The method of claim 9 wherein the water can be combined with other solvents capable of dissolving the chlorite ion source, the chloride ion source and the chlorate ion source.

11. The method of claim 9 wherein said source of chlorite ions is an alkali metal chlorite, said source of chloride ions is an alkali metal chloride and said source of chlorate ions is an alkali metal chlorate.

12. The method of claim 9 wherein said alkali metal chlorite is sodium chlorite, said alkali metal chloride is sodium chloride and said alkali metal chlorate is sodium chlorate.

13. The method according to claim 9 wherein said composition additionally includes a material to retard the formation of chlorine dioxide, the material being selected from the group consisting of peroxides, borates, perborates, and percarbonates.

14. The method of claim 13 wherein said material is hydrogen peroxide.

15. The method of claim 9 wherein the mol ratio of said chlorite ion to said chlorate ion is in the range of about 3:1 to about 500:1, mol ratio of said chlorite ion to said chloride ion is in the range of about 1:1 to about 50:1 and said chloride ion to said chlorate ion is in the range of about 3:1 to about 10:1.

* * * * *